United States Patent [19]

Forester

[11] 4,248,634

[45] Feb. 3, 1981

[54] PRESERVATIVE SOLUTIONS CONTAINING SODIUM DEHYDROACETATE WITH OR WITHOUT SODIUM BORATE DECAHYDRATE AND/OR DISODIUM EDETATE

[76] Inventor: John Forester, 2816 Assiniboine Ave., Winnipeg, Manitoba, Canada, R3J 0B1

[21] Appl. No.: 36,131

[22] Filed: May 4, 1979

[30] Foreign Application Priority Data

May 26, 1978 [CA] Canada .................................. 304230

[51] Int. Cl.³ ...................... C09D 5/14; A01N 59/14
[52] U.S. Cl. ............................... 106/15.05; 252/408; 424/148; 424/153
[58] Field of Search ..................... 106/15.05; 252/408; 424/148, 153

[56] References Cited

U.S. PATENT DOCUMENTS 3,962,125  6/1976  Armstrong .......................... 252/408

*Primary Examiner*—Maurice J. Welsh
*Attorney, Agent, or Firm*—Stanley G. Ade

[57] ABSTRACT

Sodium azide is used as a preservative or bacteriostatic agent of various solutions such as hypertonic phosphate solution, cleaning solutions used in electronic counting equipment, Sorensen's phosphate buffers, lytic agents E and F and the like. Unfortunately, sodium azide, when combined with lead or copper in sink plumbing can produce explosive substances and also is capable of generating toxic gases. By using sodium dehydroacetate with or without sodium borate decahydrate and/or disodium edetate, the disadvantages are removed and at the same time the efficiency of the various solutions is not affected adversely.

11 Claims, No Drawings

PRESERVATIVE SOLUTIONS CONTAINING SODIUM DEHYDROACETATE WITH OR WITHOUT SODIUM BORATE DECAHYDRATE AND/OR DISODIUM EDETATE

BACKGROUND OF THE INVENTION

This invention relates to new and useful improvements in solutions containing sodium dehydroacetate with or without sodium borate decahydrate and/or disodium edetate.

The solutions are used as blood diluents for blood cell counting and sizing, and for use in hematological enumeration of blood cells and the determination of hemoglobin concentration by electronic particle analysis using a Coulter hemoglobinometer or similar automated cell (particle) counter.

The sodium azide acts as a preservative without altering the characteristics of the diluent in any way, but unfortunately it has certain undesirable features which are eliminated by the present invention.

One undesirable feature in the use of sodium azide as the effective bacteriostatic agent, is that it is relatively highly toxic so that aqueous solutions of sodium azide and vapours of hydrozoic acid can possibly contribute to adverse effects on laboratory workers if exposed to same. Furthermore, in the case of plumbing systems using copper and lead pipes and joints through which such solutions must be drained, it is necessary to exercise careful flushing procedures in order to prevent excess accumulations of heavy metal azides over extended periods of time, such excess accumulations sometimes leading to the formation of explosive conditions.

An attempt has been made to substitute other preservatives for sodium azide and an example of this is shown in U.S. Pat. No. 3,962,125 which uses, as a bacteriostatic agent, 2-phenoxyethanol. This agent is substantially less toxic than sodium azide and therefore eliminates the problems enumerated above. Unfortunately, however, it is necessary to use a percentage of sodium fluoride in such solutions containing 2-phenoxyethanol and the use of sodium fluoride has been found to have an etching effect on glass and related substances and therefore causes early deterioration of glass tubes and connections in scientific equipment, requiring frequent replacement of parts at considerable cost to the user.

Furthermore, sodium fluoride is classified as a very toxic substance (toxicity level 4-5 on a maximum scale of 6) see Clinical Toxicology of Commercial Products, Gosselin et al, editors, The Williams and Wilkins Company, Baltimore Fourth Edition, 1976, page 78. Indeed, 0.25-0.45 grams of sodium fluoride will cause severe toxic symptoms including nausea, vomiting, abdominal distress, diarrhea, stupor and weakness. Doses of only 4.0 grams will cause death. In this context, it is to be noted that sodium fluoride is being used as an insecticide for roaches and ants and in other pesticide formulations. (Martindale, The Extra Pharmacopoeia 27th edition, The Pharmaceutical Press, London, 1977, page 618; also see Clinical Toxicology of Commercial Products, above). It should be noted also that the long term genetic and cancer causing effects of all insecticides are currently under suspicion and review. Indeed, fluorides have been implicated specifically as carcinogenic agents.

In invention U.S. Pat. No. 3,962,125 sodium fluoride is said to be required to aid the conversion of hemoglobin to cyanmethemoglobin but the following also should be noted: (1) sodium fluoride is known as an excellent preservative of blood (Med J. Aust. 1:1939, 1968) and (2) Phenoxyethanol, the substance listed as the preservative in U.S. Pat. No. 3,962,125, is a rather poor preservative in its own right and is more effective when used in conjunction with other preservatives, such as the hydroxybenzoates (The Extra Pharmacopoeia, ibid page 1281). Similar co-operative effects can be expected for other preservatives such as fluorides but have, to my knowledge, not been specifically investigated.

It should be noted also that phenoxyethanol is a rather weak antimicrobial agent, being most effective against *Pseudomonas aeruginosa,* but less effective against *proteus vulgaris,* other gram negative organisms and gram positive organisms, even when used in concentrations 3 times as great as those of invention U.S. Pat. No. 3,962,125 (The listed concentration of 3.3 grams/liter is equivalent to a 0.33% solution, considering that phenoxyethanol is a liquid with a weight per ml of 1.105; usually a 1% solution is considered optimal for preservative use) see The Extra Pharmacopoiea, ibid, page 1281. In addition, phenoxyethanol carries a toxicity rating of 4 on a maximum scale of 6. See Clinical Toxicology of Commercial Products, ibid, page 123, item 424.

SUMMARY OF THE INVENTION

The present invention overcomes these disadvantages by utilizing sodium dehydroacetate* with or without sodium borate decahydrate and/or disodium edetate** and one aspect of the invention is to provide a multi-purpose solution for use in automated cell (particle) counters, as a cleaning solution in hemoglobinometry and cleaning solutions used on all types of automated cell counters (particle counters) and with a lytic agent concentrate, and the like, consisting essentially of:
  (a) an osmotically balance solution of sodium chloride, potassium chloride, sodium phosphate dibasic and sodium phosphate monobasic, and:
  (b) sodium dehydroacetate, said solution being an aqueous electrolyte solution wherein the sodium dehydroacetate is bacteriostatic in nature.

*Sodium dehydroacetate is a sodium salt with the following structural formula:

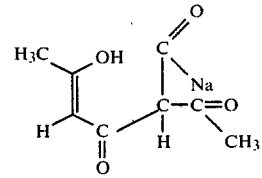

**Disodium edetate is a tetraacetic acid disodium salt having the structural formula:

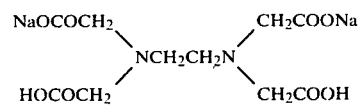

The solution may be used under a variety of conditions and some of these conditions are as follows:
1. Replacement of sodium azide used as a preservative of hypertonic phosphate solutions. sodium azide, when combined with lead or copper in sink plumbing becomes explosive.
2. To be used to preserve and stabilize red blood cells in hypertonic buffered phosphate solutions.
3. To be used in all types of automated particle counters with special emphasis on red blood cell, white cell, and platelet counting.
4. To be used to preserve cleaning solutions used in electronic counting equipment.
5. To preserve Sorensen's phosphate buffers used with Wright's stain solution for blood staining purposes.
6. To be used to preserve hypertonic cleaning solutions which are used on all types of automated particle counters.
7. To be used to preserve lytic agents E and F which are vital in blood cell counting procedures.

Both sodium dehydroacetate and sodium borate are relatively inert products that do not attack glass, plastics or other products commonly used in scientific equipment. The use of these products for over three years in equipment has lead to no noticeable deterioration. This situation is in stark contrast to that seen with the use of sodium fluoride containing products.

Sodium dehydroacetate has minimal toxicity (class 3 product)—see Clinical Toxicology of Commercial Products as above page 202. Indeed, sodium dehydroacetate is commonly used as a food preservative and as a stabilizer and preservative of cosmetic products. As such, it enjoys long standing approval by the FDA. Ingestion by human subjects of doses as high as 0.01 grams/kilogram/day (i.e. approximately 0.5–1.0 grams/day) for 150 days has produced no observable ill effects. The $LD_{50}$ in rats is very high at 1 gram/kilogram. There is no evidence to link this class of product with genetic or cancer causing potential.

Similarly, sodium borate decahydrate is classed as being at toxicity level 3—see Clinical Toxicology of Commercial Products as above page 82. This product also has not been linked with genetic or cancer causing potential.

Unlike sodium azide, neither sodium dehydroacetate nor sodium borate decahydrate form explosive heavy metal azides when coming in contact with lead or copper drainage pipes or plumbing. No toxic vapors are generated that might affect laboratory workers adversely.

Other advantages of these products are as follows: For instance
(a) the diluent is unreactive and osmotically balanced.
(b) the diluent is capable of conducting current.
(c) there are no adverse effects on white blood cells and platelets.
(d) the diluent does not require special procedures for its formulation, etc.

With the foregoing in view, and other advantages as will become apparent to those skilled in the art to which this invention relates as this specification proceeds, my invention consists essentially in the arrangement as hereinafter more particularly described.

DETAILED DESCRIPTION

Given below is a suggested formulation of a hypertonic phosphate solution used in automated cell (particle) counters.

I.
a. Sodium chloride: 0.8%–0.83%
b. Sodium phosphate dibasic: 0.170%–0.175%
c. Sodium phosphate monobasic: 0.029%–0.035%
d. Potassum chloride: 0.038%–0.040%
e. Sodium borate decahydrate: 0.06%–0.10%
f. Disodium edetate: 0.1%
g. Sodium dehydroacetate: 0.15%–0.85%

II. As above (I) but, without disodium edetate.

III. As above (I), but without sodium borate decahydrate.

Special Note pH of Solution AI: should be adjusted between 7 and 8 and preferably to 7.36 with concentrated phosphoric acid.

pH of Solution AII: should be adjusted between 7 and 8 and preferably to 7.36 with concentrated phosphoric acid.

pH of Solution AIII: should be adjusted between 7 and 8 and preferably to 7.36 with sodium hydroxide.

The solution is readily adaptable for use as phosphate buffers (pH 6.4–6.9) used with Wright's staining solution for blood staining purposes.

Monopotassium phosphate: 0.08%–0.098%
Disodium phosphate: 0.062%–0.072%
Sodium dehydroacetate: 0.045%–0.50%

It has also been found that the solution is readily adapted for use as a cleaning solution used in hemoglobinometry (Coulter hemoglobinometer) and related instruments in which the sodium dehydroacetate is mixed with sodium chloride and a non-ionic surfactant such as Brij 35 (registered trade mark) and an example of this is as follows:
(a) Sodium chloride: 0.1%
(b) Brij 35*: 0.1%
(c) Sodium dehydroacetate: 0.5%

*Brij is a registered trade mark of ICI Americas for a nonionic surfactant Polyoxyethylene (23) Lauryl Ether.

In the hypertonic phosphate solution mentioned above, sodium borate decahydrate prevents spotting on glassware of electronic devices and the sodium dehydroacetate not only stabilizes blood cells, but also acts as a preservative or bacteriological agent.

A further excellent hypertonic cleaning solution which can be used on all types of automated cell counters (particle counters) can be made with the aforementioned hypertonic phosphate solution with or without disodium edetate and/or sodium borate decahydrate, together with any combination of a non-ionic surfactant such as Triton X-100* (registered trade mark), Brij 35 (registered trade mark) or Triton CF-54** (registered trade mark), utilizing approximately 0.1% thereof by volume.

*Triton X-100 is a registered trade mark of Rohm and Haas, Philadelphia of an alkylarylpolyether alcohol with the "x" value representing the average number of ethylene oxide units in the ether side chain of the product.
**Triton CF-54 is a registered mark of Rohm and Haas for a nonionic surface-active agent described as a modified polyethoxy adduct.

A lytic agent concentrate can be utilized usuable on all types of automated blood cell counters except the Coulter Counter model "S." This agent lyses red blood cells and prevents the white blood cells, to be counted, from lysing. The lytic agent also converts all forms of hemoglobin to cyanmethemoglobin which can be estimated in photoelectric colorimeters. The density of the color produced is directly proportional to the amount of hemoglobin in man and animals.

The procedure is as follows:

To 0.02 ml to 0.05 ml of blood diluted in 10 ml of the aforementioned hypertonic phosphate solutions, 3 to 6 drops of lytic agent is added. The lysing action and conversion of hemoglobin occurs in seconds.

The formula for the lytic agent is as follows:

|  | 1 liter of lytic agent E |
|---|---|
| A. Potassium cyanide | 3.2 g |
| B. Cetyl trimethyl ammonium bromide | 78.0 g |
| C. Glycerol USP | 110.0 ml | with sufficient hypertonic phosphate solution to make up one liter. The hypertonic phosphate solution can either be the basic solution described with or without disodium edetate and with or without sodium borate decahydrate.

The pH of this lytic agent is adjusted to between 7 and 8 with concentrated phosphoric acid with the preferred pH being 7.4.

A further formula is given for lytic agent F. This lytic agent is used only on one type of electronic self-counter, namely the Coulter Counter Model "S" and the principles are similar to those described in lytic agent E. In this particular agent, 0.25 g potassium cyanide is mixed with 20.0 g of cetyl trimethyl ammonium bromide and sufficient of the hypertonic phosphate solution is used to bring the quantity up to one liter.

Once again the pH of this agent is adjusted with phosphoric acid as hereinbefore described.

Finally, the characteristics of the hypertonic phosphate solution hereinbefore described include the fact that the blood cells are stable in the solution for several hours and the stability of hypertonic solution preserved with sodium dehydroacetate is at least 10 months at room temperature.

Since various modifications can be made in my invention as hereinabove described, and many apparently widely different embodiments of same made within the spirit and scope of the claims without departing from such spirit and scope, it is intended that all matter contained in the accompanying specification shall be interpreted as illustrative only and not in a limiting sense.

What I claim as my invention is:

1. A multi-purpose hypertonic phosphate solution for use in automated cell counters, as a cleaning solution in hemoglobinometry and cleaning solutions used on all types of automated cell counters with a lytic agent concentrate consisting essentially of:

(a) an osmotically balanced solution of sodium chloride, potassium chloride, sodium phosphate dibasic and sodium phosphate monobasic, and:
   (b) sodium dehydroacetate, said solution being an aqueous electrolyte solution wherein the sodium dehydroacetate is bacteriostatic in nature.

2. The solution according to claim 1 which includes disodium edetate.

3. The solution according to claim 1 which includes sodium borate decahydrate.

4. The solution according to claim 2 which includes sodium borate decahydrate.

5. The solution according to claim 1 in which the approximate proportions by volume comprise sodium chloride 0.8% to 0.83%, sodium phosphate dibasic 0.170% to 0.175%, sodium phosphate monobasic 0.029% to 0.035%, potassium chloride 0.038% to 0.040%, and the sodium dehydroacetate 0.45% to 0.50%.

6. The solution according to claim 5 which includes disodium edetate in the proportion of approximately 0.1% by volume.

7. The solution according to claim 5 which includes sodium borate decahydrate in the proporation of 0.06% to 0.10%.

8. The solution according to claim 6 which includes sodium borate decahydrate in the proportion of 0.06% to 0.10%.

9. The solution according to claims 1, 2 or 3 together with a lytic agent concentrate, said lytic agent concentrate comprising approximately 3.2 grams of potassium cyanide, 78.0 grams of cetyl trimethyl ammonium bromide, approximately 110.0 ml of glycerol USP, with said solution making up the amount of one liter.

10. The solution according to claims 1, 2 or 3 together with a lytic agent concentrate, said lytic agent concentrate comprising approximately 0.25 grams of potassium cyanide, 20.0 grams of cetyl trimethyl ammonium bromide, with said solution making up a volume of one liter, the pH being adjusted to approximately 7.4 with concentrated phosphoric acid.

11. The solution according to claims 1, 2 or 3 together with a non-ionic surfactant selected from the group comprising Triton X-100, Brij 35 and Triton CF-54, said non-ionic surfactant comprising approximately 0.1% by volume of the total.

* * * * *

UNITED STATES PATENT AND TRADEMARK OFFICE
CERTIFICATE OF CORRECTION

PATENT NO. : 4,248,634
DATED : February 3, 1981
INVENTOR(S) : John Foerster

It is certified that error appears in the above—identified patent and that said Letters Patent is hereby corrected as shown below:

On the cover sheet Item (76) Inventor name should read

-- John Foerster --.

Signed and Sealed this

Twenty-eighth Day of April 1981

[SEAL]

Attest:

RENE D. TEGTMEYER

Attesting Officer

Acting Commissioner of Patents and Trademarks